US009029582B2

(12) United States Patent
Castillo et al.

(10) Patent No.: US 9,029,582 B2
(45) Date of Patent: May 12, 2015

(54) PHARMACEUTICAL COMPOSITION

(75) Inventors: Jose Castillo, Santa Fe (AR); Jose B. Iturraspe, Santa Fe (AR); Jose L. Nunez, Entre Rios (AR)

(73) Assignee: Capital, Business Y Gestion de Finanzas S.L., Madrid (ES)

( * ) Notice: Subject to any disclaimer, the term of this patent is extended or adjusted under 35 U.S.C. 154(b) by 0 days.

(21) Appl. No.: 14/117,958

(22) PCT Filed: Apr. 23, 2012

(86) PCT No.: PCT/ES2012/070267
§ 371 (c)(1),
(2), (4) Date: Nov. 15, 2013

(87) PCT Pub. No.: WO2012/160223
PCT Pub. Date: Nov. 29, 2012

(65) Prior Publication Data
US 2014/0088061 A1    Mar. 27, 2014

(30) Foreign Application Priority Data

May 20, 2011  (AR) ............................... P110101751
Sep. 20, 2011  (AR) ............................... P110103435

(51) Int. Cl.
*C07J 1/00* (2006.01)
*A61K 31/56* (2006.01)
*A61K 31/565* (2006.01)
*A61K 9/00* (2006.01)
*A61K 9/19* (2006.01)

(52) U.S. Cl.
CPC ............ *A61K 31/565* (2013.01); *A61K 9/0019* (2013.01); *A61K 9/19* (2013.01)

(58) Field of Classification Search
None
See application file for complete search history.

(56) References Cited

U.S. PATENT DOCUMENTS

2007/0116729 A1    5/2007 Palepu

FOREIGN PATENT DOCUMENTS

| WO | WO-0151056 A1 | 7/2001 | |
| WO | WO-2007033434 A1 | 3/2007 | |
| WO | WO 2007033434 A1 * | 3/2007 | ........... A61K 31/565 |
| WO | WO-2009012283 A1 | 1/2009 | |

OTHER PUBLICATIONS

Petit, Polymorphism in the Pharmaceutical Industry,. Wiley, 2006, p. 259-285.*
International Search Report issued in PCT/ES2012/070267, dated Jul. 17, 2012.

* cited by examiner

*Primary Examiner* — Dennis Heyer
*Assistant Examiner* — Daniel M Podgorski
(74) *Attorney, Agent, or Firm* — Locke Lord LLP; Nicholas J. DiCeglie, Jr.

(57) ABSTRACT

The invention relates to a solid pharmaceutical composition comprising solid amorphous fulvestrant, said composition being formulated in combination with a solubilizing composition. The invention also relates to a method for preparing said composition and a kit including the composition.

12 Claims, 9 Drawing Sheets

PHARMACEUTICAL COMPOSITION

CROSS REFERENCE TO RELATED APPLICATIONS

This application is a 371 U.S. National Phase Application of PCT/ES2012/070267, filed Apr. 23, 2012, which claims priority to Argentina Patent Application No. P20110101751, filed May 20, 2011, and Argentina Patent Application No. P20110103435, filed Sep. 20, 2011, the disclosures of each of which are expressly incorporated herein by reference in their entireties.

TECHNICAL FIELD

The present invention refers to the field of pharmaceutical compositions, especially pharmaceutically active substances of poor solubility in aqueous media, specifically oncological products such as fulvestrant.

BACKGROUND

Fulvestrant, or 7-alpha-[9-(4,4,5,5,5-pentafluoropentyl-sulphonyl)nonyl]estra-1,3,5-(10)-triene-3,17-beta-diol taught by Patent GB 8327256 in 1983, is a white powder having a molecular weight of 606.77. Fulvestrant is the active principle of the commercial product Faslodex, AstraZeneca. Faslodex is commercialized as a composition to be preserved at refrigerator temperature in the form of an oily injectable solution containing 250 mg fulvestrant dissolved in 5 mL solvent. The solvent comprises 10% w/v ethyl alcohol, 10% w/v benzyl alcohol, 15% w/v benzyl benzoate and a sufficient amount of castor oil to complete 100% w/v (8).

Fulvestrant is indicated for the treatment of post-menopausal women with locally advanced or metastatic breast cancer and with positive estrogenic receptor, where the disease has relapsed during or after adjuvant treatment with antiestrogens or where the disease has progressed during antiestrogen treatment (8).

Faslodex is provided in prefilled sterile syringes for a single patient containing 50 mg/mL fulvestrant whether as a single 5 mL injection or as two concurrent 2.5 mL injections for administering a monthly dose. Faslodex is administered as an intramuscular injection of 250 mg once a month (8).

The present invention consists of a solid fulvestrant composition having enhanced solubility characteristics as compared to the solubility of the solid active principle, which is achieved by solubilization of fulvestrant in a lyophilization solvent and a drying process, preferably lyophilization. This new composition is capable of being commercialized as a dry powder, separately from a solubilizing composition to be mixed before the injection. This new formulation comprising said solid composition and said solubilizing composition provide greater stability, as the solid is less reactive than the solution. The preferred form of the present invention is an amorphous fulvestrant solid, more preferably lyophilized.

US 2007/0116729 describes, in claim 1, a method of lyophilization comprising two stages: first the material is dissolved in a solvent for said material to form a solution or to make a slurry of the material and pH is adjusted to dissolve the drug to form a solution; then a non-solvent is added for said material to said solution, wherein the non-solvent is miscible with said solvent to force said material at least partially out of said solution, and wherein said non-solvent is vaporizable under freeze-drying conditions. In claim 4 of said document it is established that if the material is hydrophobic and/or lipophylic said solvent is selected from the group consisting of 5 to 7-membered heteroring systems and claim 5 mentions that the solvent of claim 4 is selected from the group of tetrahydrofuran, tetrahydropyran, dioxane, and trioxane. In claim 44 of said document fulvestrant is mentioned. As indicated in this document, when the materials are lipophylic the solvent is selected from the group consisting of 5 to 7-membered heteroring systems. The present invention employs acetic acid, dimethylsulfoxide, or tert-butanol all of which have the following advantages: melting point from 15 to 25° C. which favors the lyophilization process, are considered as solvents of very low toxicity and minor risk for human health (class 3 solvents according to ICH (9)) and accordingly they are suitable for pharmaceutical use. By contrast, tetrahydrofuran has a melting point of −108 C, which hinders or prevents its solidification and hence its lyophilization; further, together with dioxane they are recommended as solvents of limited use in pharmaceutical products, both being solvents class 2 according to ICH. There is no information on tetrahydropyran and trioxane solvents in pharmaceutical products nor are they present in the list of residual solvents of ICH. Further, the non-solvent mentioned in this patent document is included in the group of mono-, di- or tri-hydro alcohols of 1 to 4 carbon atoms, and it should be noted that fulvestrant is highly soluble in ethanol (3) and in tert-butanol (7) so that on the contrary of what is established in this document they could not be used as non-solvents; in the present invention the non-solvent is water. Furthermore, US 2007/0116729 claims a solvent selected from the group of liquid polyethylene glycols and propylene glycol as a lyophilization solvent; it is noted that according to (7) fulvestrant solubility in propylene glycol is 4 mg/ml, and that its solubility in polyethylene glycol 400 is 22.5 mg/mL; considering that for therapeutic purposes 250 mg of fulvestrant should be administered in a volume of less than or equal to 5 mL which is the maximum volume recommended for intramuscular injection (3), when using these solvents at least 62.5 mL and 11 mL of propylene glycol and polyethylene glycol 400, respectively, would be required, which makes these solvents inadequate for use in a sustained-release pharmaceutical product comprising Fulvestrant to be administered intramuscularly or subcutaneously; in the latter route of administration only up to 3 milliliters may be administered (9). The solid pharmaceutical composition of fulvestrant of the present invention, at a concentration of at least 50 mg/mL, is dissolved in a solvent comprising castor oil and mixtures of alcohols, over a period of less than 2 minutes, which makes it suitable as a pharmaceutical product, further presenting the advantage of a greater chemical stability as a function of temperature over Faslodex, and since the manufacture process of the lyophilizate is carried out in an oxygen-free environment, where oxygen is responsible of oxidation of fulvestrant into a sulphone fulvestrant impurity, the formulation of the present invention may be stored without stability concerns at 25° C., whereas Faslodex must be stored at 2 to 8 C. Thus, the composition of the present invention does not need to be stored in a refrigerator in climatic zones I and II, as is the case of Faslodex.

U.S. Pat. No. 6,774,122 discloses a method for the treatment of breast or reproductive tract diseases comprising administering an injection containing fulvestrant in a carrier of ethanol, benzyl alcohol, benzyl benzoate, and castor oil. Said document teaches that although fulvestrant is significantly more soluble in castor oil than in any other tested oil, it may not be dissolved only in an oil-based solvent to achieve a sufficiently high concentration for administering a low-volume injection to a patient and obtain a therapeutically significant release rate. This problem is solved by the addition of organic solvents in which fulvestrant is very soluble and which are soluble in castor oil as an alcohol, and it was found by adding a non-aqueous ester-type solvent miscible with castor oil, together with these organic solvents, surprisingly a solubility of at least 50 mg/mL of fulvestrant was achieved. Also said document describes a flowchart of the manufacturing process characterized by the following steps: fulvestrant is mixed with alcohol and benzyl alcohol and stirred until it is completely dissolved. Benzyl benzoate is added, then castor oil up to the established final weight and the solution is stirred. This manufacturing sequence is required, as a rapid dissolution of fulvestrant in castor oil is not achieved, even if it contains an alcohol. By first adding solvents capable of solubilizing it and castor oil at the end, a high concentration of active is ensured. Fulvestrant solubility in these solvents is described in the same document, establishing that fulvestrant is a particularly lipophylic molecule, even when compared to other steroidal compounds.

U.S. Pat. No. 7,456,160, which is a continuation of U.S. Pat. No. 6,774,122, extends the percentage range of the constituents of the fulvestrant solution to a range from 10 to 30% w/v of ethyl alcohol and benzyl alcohol, a range from 10 to 25% w/v of benzyl benzoate and sufficient castor oil to complete 100% w/v.

U.S. Pat. No. 5,183,814, which mentions fulvestrant as a pure antiestrogen, describes a liquid formulation containing 50 mg of fulvestrant dissolved in 400 mg of benzyl alcohol and a sufficient amount of castor oil to complete 1 mL solution. The use of a solid composition is not suggested.

PCT/GB02/03092 describes certain liquid fulvestrant formulations, preferably at 100 mg/mL. The formulations contain at least 10% w/v or more of an alcohol, 5% w/v or more of a non-aqueous ester and 5% w/v or more of a ricinoleate excipient.

EP 1409021 describes in detail a liquid formulation containing fulvestrant, a ricinoleate excipient, a non-aqueous ester, an alcohol, and an antioxidant. In the same document it is affirmed that the invention is based on the discovery that addition of an antioxidant may improve the stability of fulvestrant formulations. Addition of an antioxidant is not required for the composition of the present invention, firstly because it is solid and furthermore because by the end of the lyophilization process, the lyophilizer is filled with nitrogen. Once the filling is completed and before opening the lyophilizer, the vials are capped and thus the vials containing fulvestrant remain filled with nitrogen, as is common in the process of sealing pharmaceutical products, thereby reducing the risk of oxidation.

EP 1272195 discloses the use of fulvestrant for preparing a medicament for the treatment of a patient with breast cancer who had been treated previously with an aromatase inhibitor and tamoxifene but failed. The formulations described in said document are liquid solutions containing fulvestrant.

WO 2007/033434 discloses a solution containing fulvestrant and at least one pharmaceutically acceptable alcohol, propylene glycol or a polyethylene glycol and castor oil.

US 2009/0227549 discloses a liquid formulation of fulvestrant in a pharmaceutically acceptable carrier, without castor oil or castor oil derivatives.

The present invention solves the problem by providing solid fulvestrant which is soluble in a solubilizing composition, to be mixed before being injected in a mammal for the oncological treatment. Prior art solids of fulvestrant do not ensure solubility in a solution comprising alcohols and castor oil. In particular, the prior art requires a first dissolution of the active matter in an alcohol before adding castor oil. The present invention allows for obtaining solid fulvestrant suitable to be stored as a medicament at room temperature with no risk of degradation. It is known that fulvestrant is sensitive to oxidation into its sulfoxide function to produce the sulphone derivative, one of the major degradation products, and thus it is important to remove oxygen from the pharmaceutical formulations in order to improve preservation conditions and shelf life of the medicament. Full removal of oxygen in liquid formulations is a complicated process as it includes removing the oxygen from the air chamber of the packages, as well as the oxygen dissolved in the employed solvents. The present invention substantially simplifies the process of oxygen removal because at the end of the lyophilization process the product is in a chamber under very high vacuum which is disrupted with a gas from which oxygen has been almost entirely removed, for example highly pure nitrogen. The process ends with the tight sealing of vials inside the lyophilization chamber and thereby the solid product will remain in an oxygen-free atmosphere throughout its shelf life.

The present invention further consists of Fulvestrant in a new solid physical state and a process for manufacturing the same, which may be adapted for large-scale commercial production, thus allowing for obtaining a pharmaceutical-grade product. This new solid state is characterized by an X-ray diffraction pattern with no defined peaks and by not having a melting point.

The present invention also provides a formulation comprising said pharmaceutical solid fulvestrant composition in combination with a solubilizing composition, said composition comprising castor oil with alcohol, in the absence of other components such as benzyl benzoate, indicated in the state-of-the-art as essential for achieving solubility of the active ingredient fulvestrant. The prior art does not describe or suggest a formulation as that of the present invention nor anticipates that fulvestrant may be soluble in a castor oil and alcohol solution in less than 2 minutes, at concentrations suitable for pharmaceutical use. This is achieved with the formulation of the present invention.

BRIEF DESCRIPTION OF THE INVENTION

Figure 1:
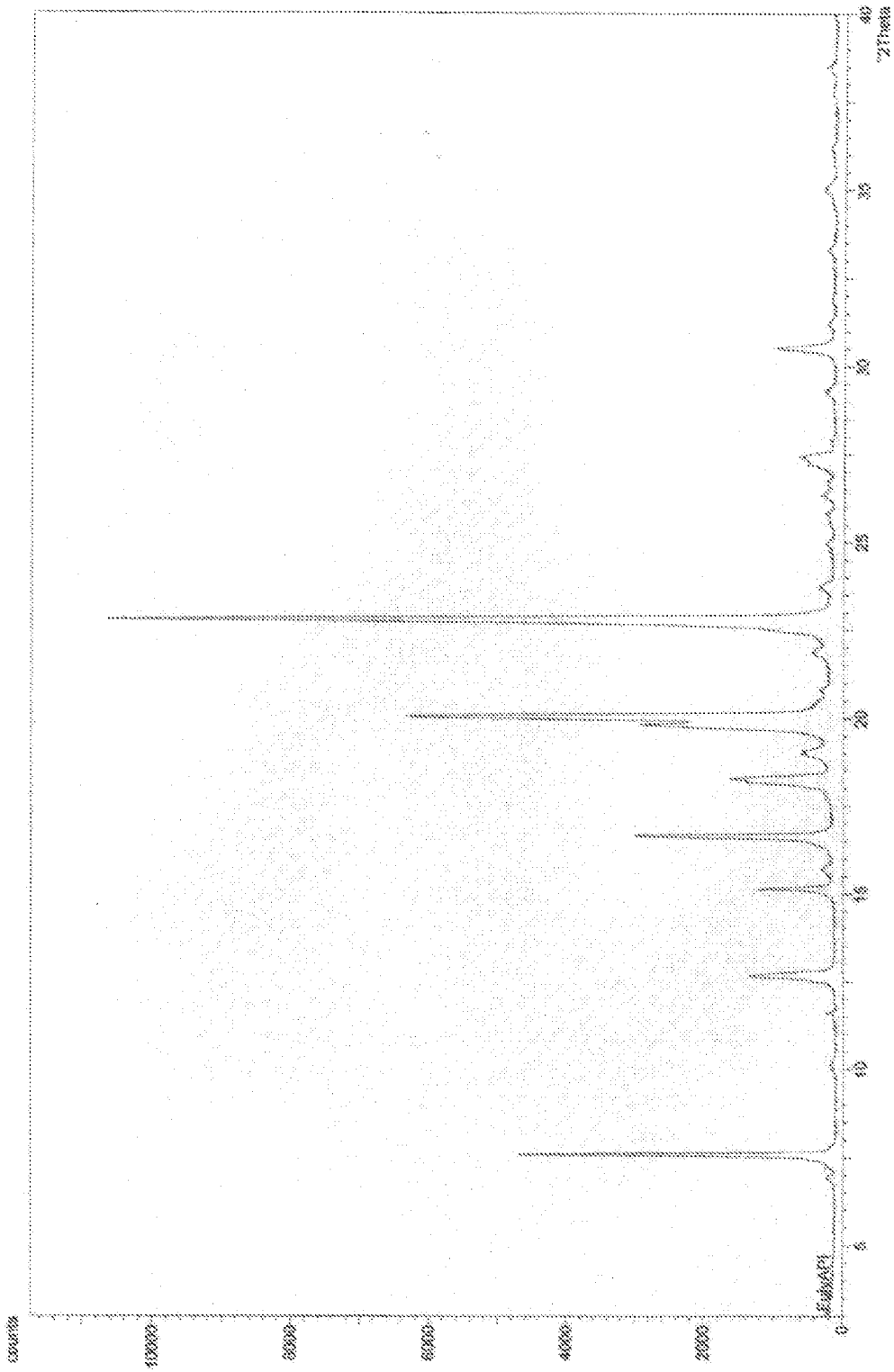
FIG. 1. X-Ray diffraction diagram of Scinopharm Fulvestrant.

The solid pharmaceutical composition of improved solubility of the present invention comprises amorphous fulvestrant. The solid composition is preferably lyophilized, even more preferably it is lyophilized from a solution of the pharmaceutical active principle fulvestrant in a lyophilization solvent selected from the group consisting of acetic acid, dimethylsufoxide, tert-butanol, and mixtures thereof. The composition further comprises an X-ray diffraction image with a maximum in a 2$\theta$ of from 15° and 20°; and selected from the group consisting of FIGS. 5 and 7. Said composition preferably comprises amorphous fulvestrant without melting point, as shown in FIGS. 6 and 8.

Furthermore said lyophilized composition is at least 95% pure. Also, said composition is soluble in a solution of castor oil, and benzyl benzoate-free alcohol, in less than 180 seconds, preferably in less than 120 seconds, more preferably less than or equal to 90 seconds.

Another object of the present invention is to provide a process for obtaining said solid pharmaceutical composition of fulvestrant comprising the steps of:

a. dissolving the active pharmaceutical principle fulvestrant in a lyophilization solvent selected from the group consisting of acetic acid, dimethylsulfoxide, tert-butanol and mixtures thereof, b. drying the resulting solution Furthermore, step b comprises freeze-drying, preferably with schedule comprising freeze-cooling the product obtained in step a to at least −20° C. for at least 5 hours, under a pressure higher than 500 mTorr. After this time has elapsed, the pressure is lowered to below 500 mTorr. After at least 3 hours, heating of the system is started with a difference of at least 5° C. between two consecutive temperatures, the heating being ramp- or step-wise and each step having an extension of at least 3 hours. Final system temperature comprises from 0 to 50° C. Preferably, a prescription as follows is used:

| Stage | Time (h) | Temperature (C.) | Vacuum |
|-------|----------|------------------|--------|
| 1 | 7 | −40 | No |
| 2 | 15 | −40 | Yes |
| 3 | 9 | −30 | Yes |
| 4 | 7 | −20 | Yes |
| 5 | 8 | −10 | Yes |
| 6 | 9 | −5 | Yes |

Furthermore, said solid pharmaceutical composition contains less than 0.5% organic solvents.

Another object of the present invention is an injectable formulation comprising said solid pharmaceutical composition of fulvestrant and a solubilizing composition. Preferably said solid composition is reconstituted with said solubilizing composition prior to being injected. Furthermore, said solubilizing composition is selected from the group consisting of ethanol, benzyl alcohol, isopropyl alcohol, polyvinyl alcohol, dimethylsulfoxide, methylparaben, polyethylene glycol, polyoxyethylated fatty acid esters, castor oil, and mixtures thereof. Preferably said solubilizing composition is selected from the group consisting of ethanol, benzyl alcohol, castor oil, and mixtures thereof. More preferably said solubilizing composition comprises ethanol, benzyl alcohol and castor oil. More preferably said solubilizing composition is free from benzyl benzoate. Preferably said castor oil is at a concentration of from 57 to 67% by weight; and said ethanol is at a concentration of up to 43% by weight; and said benzyl alcohol is at a concentration of up to 43% by weight.

Another object of the present invention is a kit comprising: a first container containing a solid composition of fulvestrant as claimed in claim 1; a second container containing a solubilizing composition for said solid fulvestrant composition; and a syringe. Preferably the syringe is prefilled and comprises said first container and said second container. The kit is useful for preparing an injectable fulvestrant formulation, suitable for preparing injections for intramuscular administration, comprising said solid fulvestrant composition of claim 1; a solubilizing composition for said solid fulvestrant composition; a syringe with a stable solution of a mixture comprising said solubilizing composition and said solid fulvestrant composition. Alternatively said kit comprises a transfer system connecting the containers to said syringe.

Another object of the present invention is the use of a transfer system which connects a vial containing the solid composition of claim 1 to another vial containing a solubilizing composition for said solid composition and to a syringe to inject the reconstituted solution formed by mixing the contents of said vials.

DETAILED DESCRIPTION OF THE INVENTION

The present invention consists of a solid fulvestrant composition showing improved solubility characteristics with respect to the solubility of the solid active principle. The problem of solubility of fulvestrant, as described in U.S. Pat. No. 6,774,122, in a solution of castor oil and at least one alcohol is solved by the addition of a non-aqueous ester-type solvent miscible with castor oil. The present invention provides a new solution to this technical problem, not by addition of a solvent, but by obtaining dried solid fulvestrant, preferably through a lyophilization process, and preferably amorphous.

Lyophilization is a drying process, in which the solvent or suspension medium are crystallized at low temperatures and then sublimated directly from solid state to vapor state (1). The problem we encountered was that fulvestrant is practically insoluble in water (3) and that the overwhelming majority of lyophilizates of pharmaceutical solutions are lyophilized from simple aqueous solutions (2). Given that fulvestrant is practically insoluble in water, it cannot be used as a lyophilization solvent. We have solved this technical problem, among others, by means of lyophilization with organic solvents or using solvent-non-solvent systems. The use of organic solvents in the lyophilization is not found in the state-of-the-art (4), and additionally the scientist should keep in mind that the use of organic co-solvent/water systems may cause a myriad of problems (2).

We have developed processes for lyophilizing fulvestrant employing pure organic solvents such as acetic acid, dimethylsufoxide and tert-butanol, and in addition solvent-non-solvent systems consisting of organic solvents and water as non-solvent, for example, acetic acid:water, ethanol:water, tert-butanol: water.

The lyophilized solid pharmaceutical compositions of fulvestrant of the present invention have solubility characteristics which are not observed for the solid pharmaceutical active principle. This improved solubility makes it suitable to be used as a pharmaceutical product of rapid dissolution but with no need of using benzyl benzoate as a solvent for castor oil.

The lyophilizate should be reconstituted within a reasonable period, typically of less than 2 minutes (5); if reconstitution time is excessive, that is, more than 3 minutes, the user may get impatient or frustrated (6). We have compared dissolution time of a fulvestrant lyophilizate to a pharmaceutical active comprising solid fulvestrant and found that the fulvestrant lyophilizate is dissolved in less than 2 minutes, whereas the pharmaceutical active of solid fulvestrant required more than 60 minutes. This comparison was performed by dissolving fulvestrant at a concentration of 50 mg/mL, using a solvent comprising castor oil and benzyl benzoate-free alcohol mixtures.

Another important fact of the present invention is that when carrying out the methods of manufacturing lyophilizates there was no variation in purity associated to the active principle used in the same, and this consideration is made keeping in mind that the method of USP 34 monograph on fulvestrant is used for determining related compounds. Furthermore, it should be noted that there was no degradation either during the process of reconstituting lyophilizates, using a solvent comprising castor oil and benzyl benzoate-free alcohol mixtures.

The lyophilizate and its reconstituted form meet the required impurity values established in the ICH guidelines for impurities in final products, thus allowing for using this product as an injectable medicament which, given the characteristics of solvents and active principle and that it is administered intramuscularly or subcutaneously, could be used as a sustained-release product of fulvestrant.

Herein, the term solid refers to non-liquid states, or solutions, but to lyophilization powders or plugs, either in a crystalline or amorphous state.

Another object of the present invention is a kit comprising two containers, one containing the solid fulvestrant, preferably lyophilized and amorphous, of the present invention and the other containing the solubilizing composition of the present invention. In a first embodiment of the kit, it comprises the containers and a syringe. In a second embodiment, it comprises a prefilled syringe containing said two containers. In a third alternative of said containers, syringe and transfer system, said transfer system connects both containers with the syringe. This third option turned out to be the most efficient, as demonstrated in the examples. The needle-free transfer system allowed for transferring the solvent to the syringe, from the syringe to the lyophilizate and then the reconstituted form to the syringe, rapidly and with a minimum effort. Furthermore, the risk of injuries to health workers due to needle manipulation, as well as product contamination, are reduced to a minimum because the solvent vial-transfer system-lyophilized vial system is a closed system. Thus, another object of the present invention is the use of a transfer system for connecting the containers containing the solubilizing composition, the container containing the solid fulvestrant of the present invention and a syringe.

Another object of the present invention is a process for obtaining the composition of claim 1 comprising the following steps of:

a. dissolving the active pharmaceutical principle fulvestrant in a lyophilization solvent selected from the group consisting of acetic acid, dimethylsulfoxide, tert-butanol and mixtures thereof, b. drying the resulting solution where preferably said solid composition containing less than 0.5% organic solvents is obtained;

where step b of said process comprises lyophilization.

Further, lyophilization comprises cooling the product obtained in step a to at least −20 C for at least 5 hours, working under a pressure higher than 500 mTorr. After this time has elapsed, the pressure is lowered to below 500 mTorr. After at least 3 hours, heating of the system is started with a difference of at least 5° C. between two consecutive temperatures, the heating being ramp- or step-wise and each step being of an extension of at least 3 hours. The final temperature of the system comprises from 0 to 50° C.

EXAMPLES

Example 1

Lyophilization of Fulvestrant from Acetic Acid

To a 100 mL beaker, fitted with a magnetic stirrer, 35 mL glacial acetic acid, Merck lot K 36685863, is added.

The beaker is placed on an IKA model MS2 Minishaker magnetic stirrer plate.

Seven hundred mg Fulvestrant from Scinopharm, lot#70850AA003 were weighed using an Ohaus model Adventurer balance.

Stirring of acetic acid is started and Fulvestrant is slowly added which is rapidly dissolved. After all Fulvestrant was added stirring is continued for 5 minutes. After this time has elapsed, stirring is stopped and the solution is dosed using a 5000 uL Eppendorf Research micropipette into 50 mL Schott type I glass vials, with a 12.5 mL volume. Vials are pre-capped with Helvoet Pharma bromobutyl lyophilization stoppers and lyophilized using a Virtis Advantage lyophilizer. The lyophilization cycle is shown in table 1.

Once the lyophilization process is completed, vials are capped and crimped with aluminum seals.

TABLE 1

| Lyophilization Cycle | | | |
| --- | --- | --- | --- |
| Stage | Time (h) | Temperature (C.) | Working pressure |
| 1 | 7 | −40 | Higher than 60 mTorr |
| 2 | 15 | −40 | Lower than 60 mTorr |
| 3 | 9 | −30 | Lower than 60 mTorr |
| 4 | 7 | −20 | Lower than 60 mTorr |
| 5 | 8 | −10 | Lower than 60 mTorr |
| 6 | 9 | −5 | Lower than 60 mTorr |
| 7 | 15 | −10 | Lower than 60 mTorr |

The lyophilizate thus obtained has a very good aspect. Titer and purity of one lyophilizate vial are analyzed by HPLC, and compared to Scinopharm Fulvestrant used in the manufacture of the lyophilizate. HPLC determinations were carried out on a Waters HPLC system with a Waters 1525 binary pump, Waters 717 autosampler, and a Waters 2996 diode array detector; the HPLC column used for determining titer and purity is an Agilent Eclipse XDB-C8 3.5 u 4.6×150 Rapid Res column; the chromatographic method corresponds to US Pharmacopeia (USP, 34 (2011)) monograph on Fulvestrant.

The titer of the lyophilizate was the same as that of Scinopharm Fulvestrant, 99.2%. Fulvestrant and lyophilizate total impurities were 0.1%.

A physical characterization of a sample of lyophilized Fulvestrant was performed. The physical characterization was made by X-ray diffraction, differential scanning calorimetry and thermogravimetric assays.

The X-ray assay was carried out in a Philips X'Pert with a PW3710 unity using CuKα radiation=1.54 A. Records were obtained in the range of 3°<2θ<40°. A step of 0.02° in 2θ was used with a time counting of 2 seconds per step.

Figure 5:
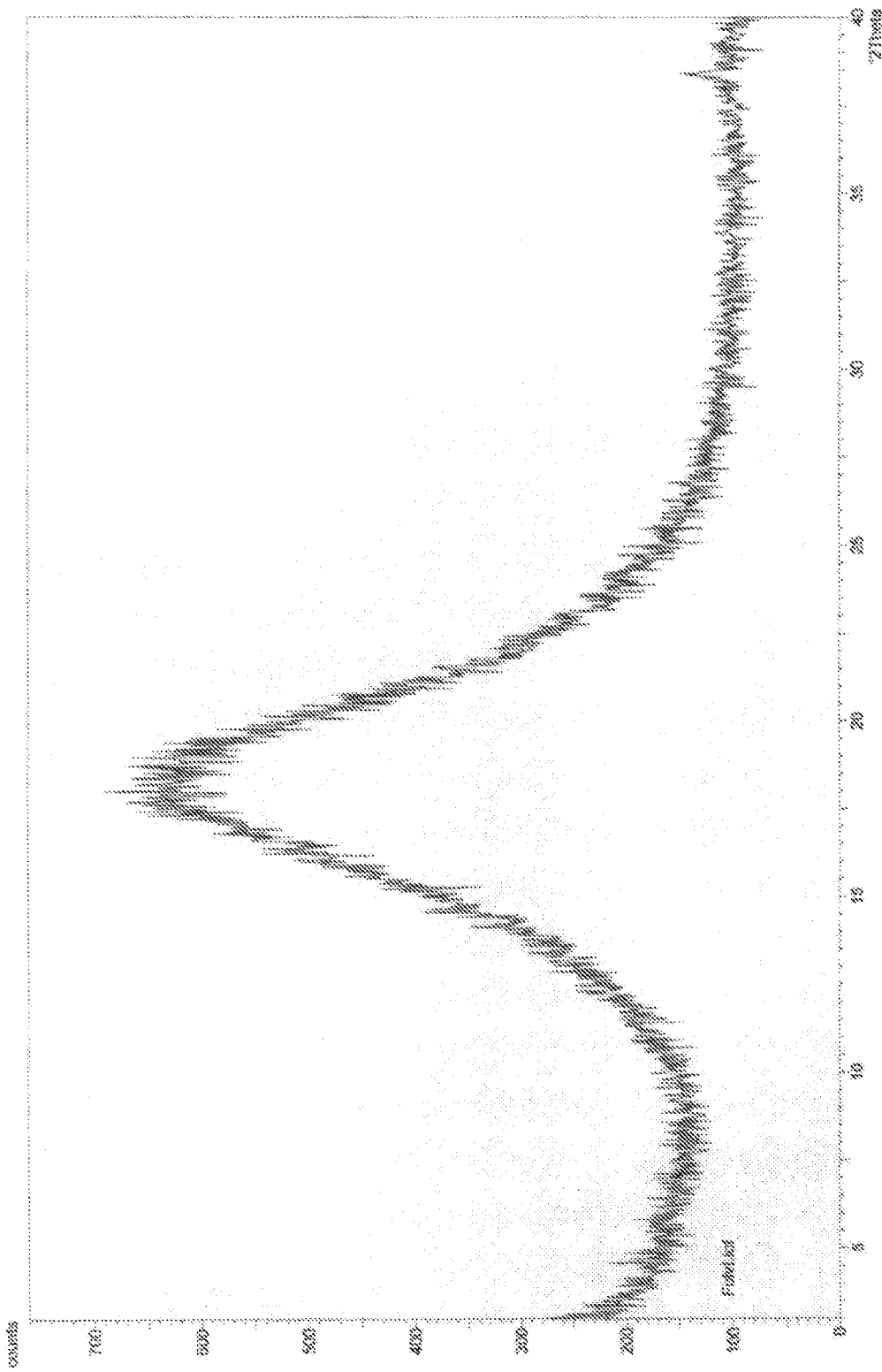
FIG. 5. X-Ray diffraction diagram of Fulvestrant lyophilized from acetic acid.
Figure 6:
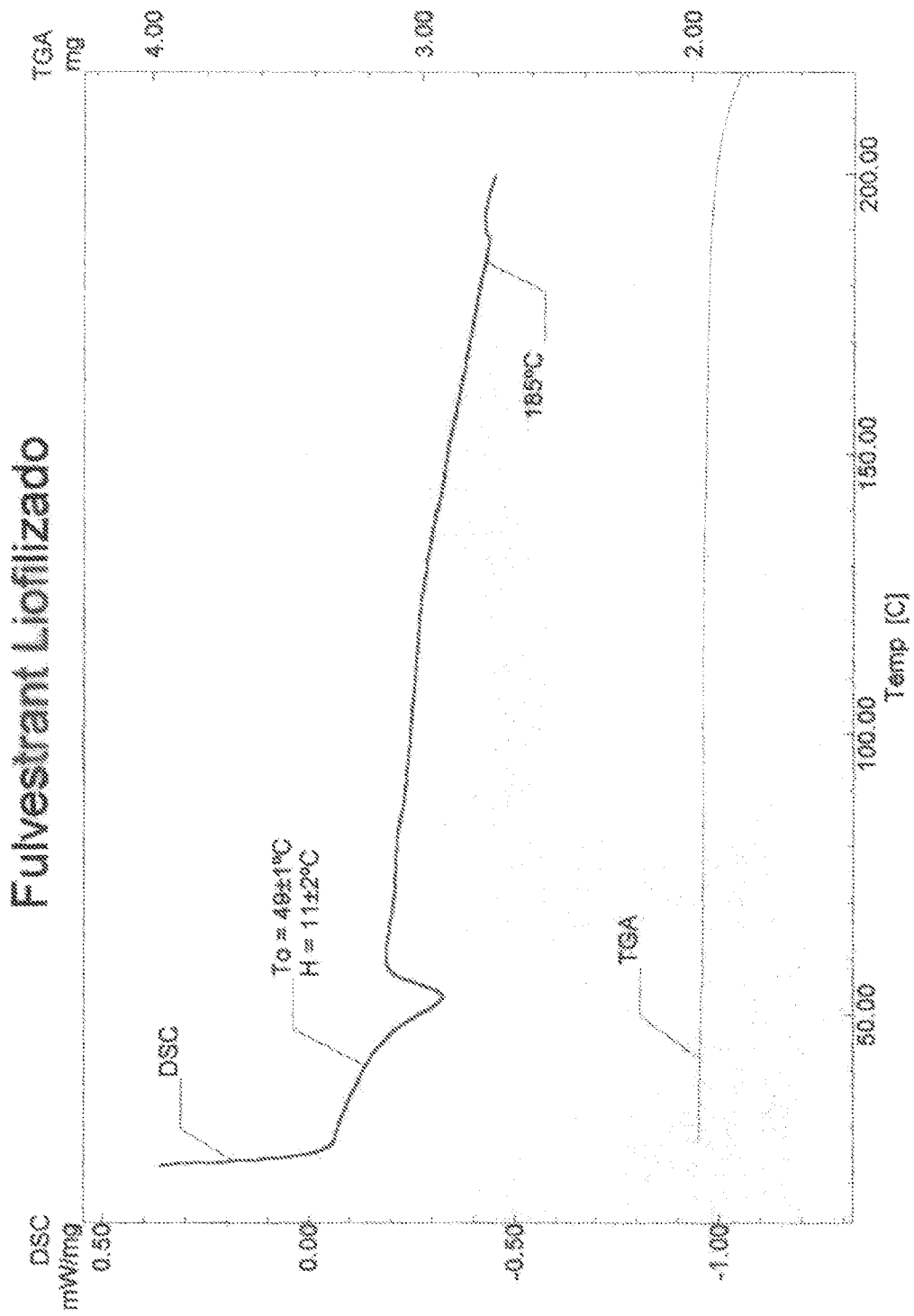
FIG. 6. Thermogram and thermogravimetry of Fulvestrant lyophilized from acetic acid.

FIG. 5 shows a diffraction diagram of the sample which has a typical diffraction pattern corresponding to an amorphous sample.

The differential scanning calorimetry assay was performed with a Shimadzu DSC 60. A sample of 2.29 mg was placed on an aluminum sampleholder, and heated at 10° C./min from room temperature to 200° C. Work was carried out under $N_2$ with a flow of 30 mL/min.

The thermogravimetric assay was performed with a Shimadzu TG 50. The sample was placed in an aluminum sampleholder. It was heated from room temperature to 400° C. with heating rate of 10° C./min, under dry air flow of 40 mL/min FIG. 6 shows a differential scanning calorimetry diagram and a thermogravimetric diagram. An endothermic signal characterized by an onset temperature To=49+/−1° C. and an enthalpy variation of 11+/−2 J/g was observed, which as may be appreciated in the thermogravimetric diagram does not correspond to mass loss.

This lyophilizate was made with Scinopharm Fulvestrant. A comparison of diffraction diagrams of the starting material, diagram 1, and the lyophilizate, diagram 5, shows that during the lyophilization process there was a transformation or change of the crystalline state of Fulvestrant from crystalline, the state of the starting material, to amorphous, the state of the lyophilized material.

When comparing the results of the thermal study of Scinopharm and Sicor Fulvestrant, it is concluded that the melting point of Fulvestrant is 102+/−2° C. and the enthalpy of fusion is 50+/−4 J/g. The lyophilizate has an endothermic signal characterized by an onset temperature To=49+/−1° C. and an enthalpy variation of 11+/−2 J/g, which is different from the crystalline Fulvestrant used for manufacturing the lyophilizate.

Example 2

Lyophilization of Fulvestrant from Tert-Butanol

To a 10 mL beaker, fitted with a magnetic stirrer, 2.5 mL of tert-butanol Tedia lot#904088 was added and then heated to 30° C.

The beaker was placed on an IKA MS2 Minishaker magnetic stirring plate, establishing plate conditions of agitation at 400 to 600 rpm and a temperature of 30° C.

Forty-nine mg Fulvestrant from Scinopharm, lot#70850AA003 were weighed using an Ohaus model Adventurer balance.

Fulvestrant is slowly added. After all Fulvestrant was added stirring is continued for 5 minutes a clear solution was obtained. After this time, stirring is stopped and with using a 5 mL syringe and needle (Darling) the solution is dosed into an 11 mL type I glass vial from Nuova Ompi. The vial is pre-capped with a Helvoet Pharma bromobutyl lyophilization stopper and lyophilized using a Virtis Advantage lyophilizator. The lyophilization cycle is shown in table 2. Once the cycle is completed, vials are withdrawn from the lyophilizator, capped and crimped with aluminum seals.

TABLE 2

Lyophilization Cycle

| Stage | Time (h) | Temperature (C.) | Working pressure |
|---|---|---|---|
| 1 | 22 | −50 | Higher than 60 mTorr |
| 2 | 6 | −50 | Lower than 60 mTorr |
| 3 | 15 | −40 | Lower than 60 mTorr |
| 4 | 9 | −30 | Lower than 60 mTorr |
| 5 | 7 | −20 | Lower than 60 mTorr |
| 6 | 11 | −10 | Lower than 60 mTorr |
| 7 | 9 | 0 | Lower than 60 mTorr |

The lyophilizate thus obtained has a very good aspect. Titer and purity of the lyophilizate is analyzed by HPLC, and compared to Scinopharm Fulvestrant used in the manufacture of the lyophilizate. HPLC determinations were carried out on an HPLC Waters with a Waters 1525 binary pump, Waters 717 autosampler, and a Waters 2996 diode array detector; the HPLC column used for determining titer and purity is an Agilent Eclipse XDB-C8 3.5 u 4.6×150 Rapid Res column; the chromatographic method corresponds to US Pharmacopeia (USP, 34 (2011)) monograph on Fulvestrant.

The titer of the lyophilizate was the same as that of Scinopharm Fulvestrant, 99.2%. Fulvestrant and lyophilizate total impurities were 0.1%.

A physical characterization of a sample of lyophilized Fulvestrant was performed. The physical characterization was made by X-ray diffraction, differential scanning calorimetry and thermogravimetric assays.

The X-ray assay was carried out in a Philips X'Pert with a PW3710 unity using CuKα radiation=1.54 A. Records were obtained in the range of 3°<2θ<40°. A step of 0.02° in 2θ was used with a time counting of 2 seconds per step.

Figure 7:
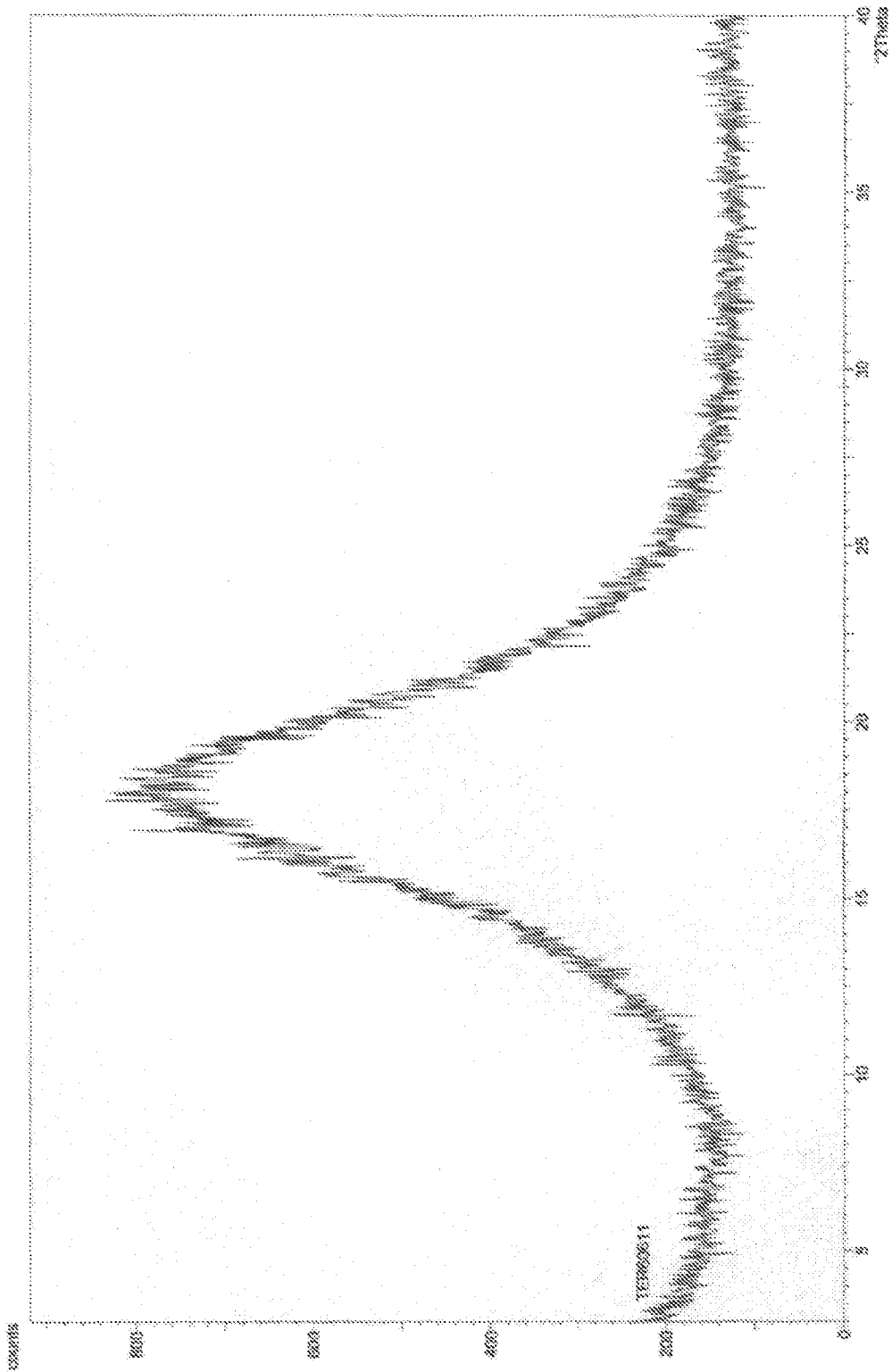
FIG. 7. X-Ray diffraction diagram of Fulvestrant lyophilized from tert-butanol.
Figure 8:
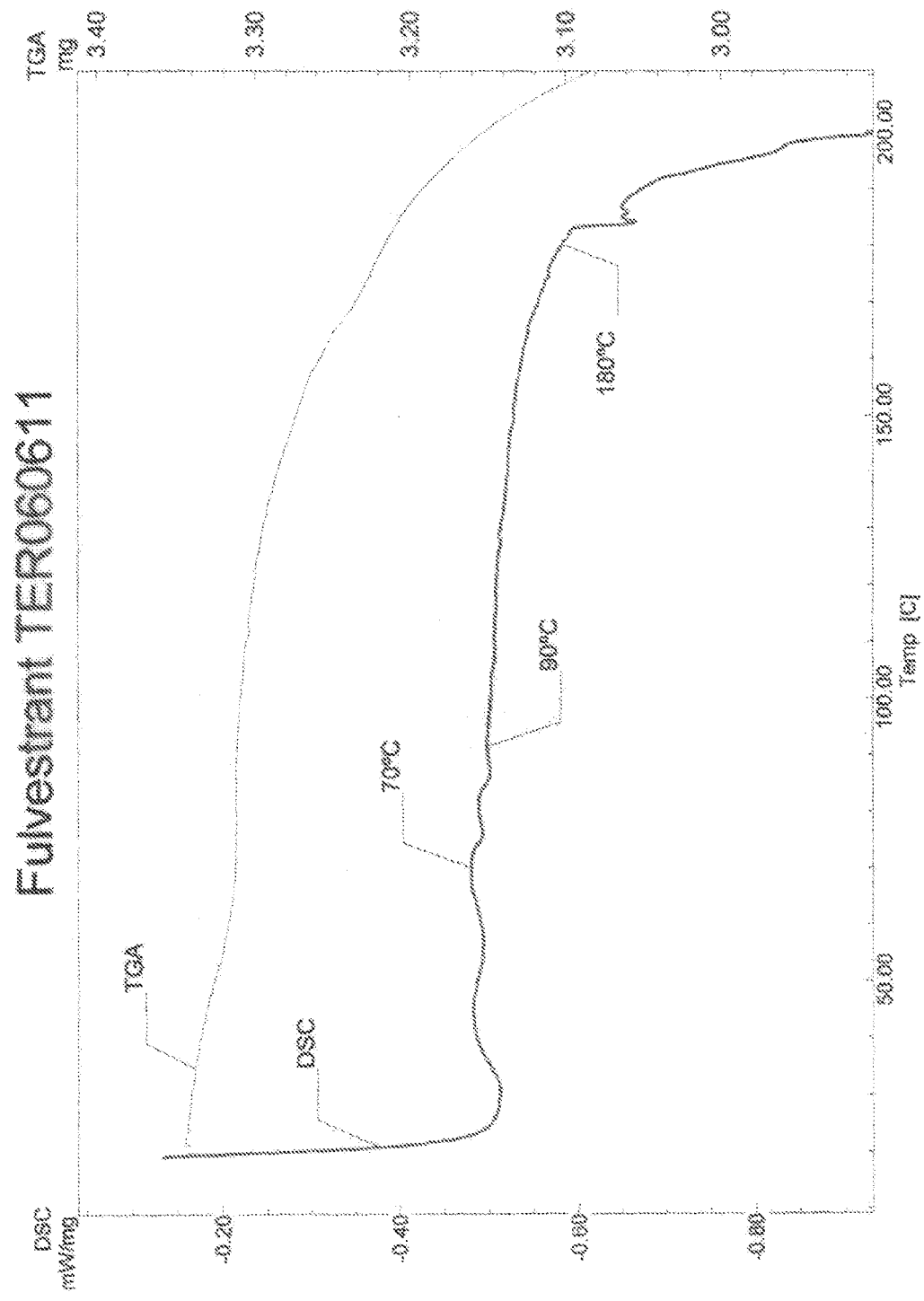
FIG. 8. Thermogram and thermogravimetry of Fulvestrant lyophilized from tert-butanol.

FIG. 7 shows a diffraction diagram of the sample which has a typical diffraction pattern corresponding to an amorphous sample.

The differential scanning calorimetry assay was performed with a Shimadzu DSC 60. A sample of 3.10 mg was placed on an aluminum sampleholder, and heated at 10° C./min from room temperature to 200° C. Work was carried out under $N_2$ with a flow of 30 mL/min.

The thermogravimetric assay was performed with a Shimadzu TG 50. The sample was placed in an aluminum sampleholder. It was heated from room temperature to 400° C. with heating rate of 10° C./min, under dry air flow of 40 mL/min FIG. 8 shows a differential scanning calorimetry diagram and a thermogravimetric diagram. Thermal signals were observed between room temperature and 70° C., probably associated with the mass loss detected by thermogravimetry. Other thermal signals were observed from 70° C. to 90° C. which apparently did not correspond to mass loss.

This lyophilizate was made with Scinopharm Fulvestrant. A comparison of diffraction diagrams of the starting material, diagram 1, and the lyophilizate, diagram 7, shows that during the lyophilization process there was a transformation or change of the crystalline state of Fulvestrant from crystalline, the state of the starting material, to amorphous, the state of the lyophilized material.

When comparing the results of the thermal study of Scinopharm and Sicor Fulvestrant, it is concluded that the melting point of Fulvestrant is 102+/−2° C. and the enthalpy of fusion is 50+/−4 J/g. The lyophilizate does not show the endothermic signals which are characteristic of phase change phenomena.

Example 3

Lyophilization of Fulvestrant from Dimethylsulfoxide

To a 50 mL beaker, fitted with a magnetic stirrer, 12.5 mL dimethylsulfoxide Malinckroff lot#904088 was added with the aid of a 5000 uL Eppendorf Research micropipette.

The beaker was placed on an IKA MS2 Minishaker magnetic stirring plate, establishing plate conditions of agitation at 400 to 600 rpm.

Two hundred and fifty mg Fulvestrant from Scinopharm, lot#70850AA003 were weighed using an Ohaus model Adventurer balance.

Fulvestrant is slowly added. After all Fulvestrant was added stirring is continued for 5 minutes a clear solution was obtained. After this time, stirring is stopped and with using a 5 mL syringe and needle (Darling) the solution is dosed into a 50 mL type I glass vial from Schott. The vial is pre-capped with a Helvoet Pharma bromobutyl lyophilization stopper and lyophilized using a Virtis Advantage lyophilizator. The lyophilization cycle is shown in table 3. Once the cycle is completed, vials are withdrawn from the lyophilizator, capped and crimped with aluminum seals.

TABLE 3

Lyophilization Cycle

| Stage | Time (h) | Temperature (C.) | Working pressure |
|---|---|---|---|
| 1 | 7 | −40 | Higher than 60 mTorr |
| 2 | 10 | −40 | Lower than 60 mTorr |
| 3 | 7 | −30 | Lower than 60 mTorr |
| 4 | 5 | −20 | Lower than 60 mTorr |
| 5 | 5 | −10 | Lower than 60 mTorr |
| 6 | 10 | −5 | Lower than 60 mTorr |
| 7 | 4 | 5 | Lower than 60 mTorr |

Example 4

Lyophilization of Fulvestrant from Acetic Acid and Water at a Ratio of 1:4 by Volume To a 5 mL beaker, fitted with a magnetic stirrer, 0.5 mL glacial acetic acid, Merck lot K 36685863 was added with the aid of a 1000 uL Eppendorf Research micropipette.

The beaker was placed on an IKA MS2 Minishaker magnetic stirring plate, establishing plate conditions of agitation at 200 to 300 rpm.

Forty-nine Mg Fulvestrant from Scinopharm, lot#70850AA003 were weighed using an Ohaus model Adventurer balance.

Fulvestrant is slowly added. After all Fulvestrant was added stirring is continued for 5 minutes a clear solution was obtained. Then, with the aid of a 5000 uL Eppendorf Research micropipette, 1 mL of water was added, and after 2 minutes additional 1 mL water was added. After the addition of water the solution is transformed into a suspension.

Stirring is stopped and with the aid of a 5 mL syringe and needle (Darling) the solution is dosed into an 11 mL type I glass vial from Nuova Ompi. The vial is pre-capped with a Helvoet Pharma bromobutyl lyophilization stopper and lyophilized using a Virtis Advantage lyophilizator. The lyophilization cycle is shown in table 4. Once the cycle is completed, vials are withdrawn from the lyophilizator, capped and crimped with aluminum seals.

TABLE 4

Lyophilization Cycle

| Stage | Time (h) | Temperature (C.) | Working pressure |
|---|---|---|---|
| 1 | 22 | −50 | Higher than 60 mTorr |
| 2 | 6 | −50 | Lower than 60 mTorr |
| 3 | 15 | −40 | Lower than 60 mTorr |
| 4 | 9 | −30 | Lower than 60 mTorr |
| 5 | 7 | −20 | Lower than 60 mTorr |
| 6 | 11 | −10 | Lower than 60 mTorr |
| 7 | 9 | 0 | Lower than 60 mTorr |

The aspect of the lyophilizate thus obtained is not good. Titer and purity of the lyophilizate is analyzed by HPLC, and compared to Scinopharm Fulvestrant used in the manufacture of the lyophilizate. HPLC determinations were carried out on an HPLC Waters with a Waters 1525 binary pump, Waters 717 autosampler, and a Waters 2996 diode array detector; the HPLC column used for determining titer and purity is an Agilent Eclipse XDB-C8 3.5 u 4.6×150 Rapid Res column; the chromatographic method corresponds to US Pharmacopeia (USP, 34 (2011)) monograph for Fulvestrant.

The titer of the lyophilizate was the same as that of Scinopharm Fulvestrant, 99.2%. Fulvestrant and lyophilizate total impurities were 0.1%.

Example 5

Lyophilization of Fulvestrant from Acetic Acid and Water at a Ratio of 1:1 by Volume To a 5 mL beaker, fitted with a magnetic stirrer, 1 mL glacial acetic acid, Merck lot K 36685863 was added with the aid of a 5000 uL Eppendorf Research micropipette.

The beaker was placed on an IKA MS2 Minishaker magnetic stirring plate, establishing plate conditions of agitation at 200 to 300 rpm.

Forty-nine Mg Fulvestrant from Scinopharm, lot#70850AA003 were weighed using an Ohaus model Adventurer balance.

Fulvestrant is slowly added. After all Fulvestrant was added stirring is continued for 5 minutes a clear solution was obtained. Then, with the aid of a 5000 uL Eppendorf Research micropipette, 1 mL of water was added. After the addition of water the solution is transformed into a suspension.

Stirring is stopped and with the aid of a 5 mL syringe and needle (Darling) the solution is dosed into an 11 mL type I glass vial from Nuova Ompi. The vial is pre-capped with a Helvoet Pharma bromobutyl lyophilization stopper and lyophilized using a Virtis Advantage lyophilizator. The lyophilization cycle is shown in table 5. Once the cycle is completed, vials are withdrawn from the lyophilizator, capped and crimped with aluminum seals.

TABLE 5

Lyophilization Cycle

| Stage | Time (h) | Temperature (C.) | Working pressure |
|---|---|---|---|
| 1 | 22 | −50 | Higher than 60 mTorr |
| 2 | 6 | −50 | Lower than 60 mTorr |
| 3 | 15 | −40 | Lower than 60 mTorr |
| 4 | 9 | −30 | Lower than 60 mTorr |
| 5 | 7 | −20 | Lower than 60 mTorr |
| 6 | 11 | −10 | Lower than 60 mTorr |
| 7 | 9 | 0 | Lower than 60 mTorr |

The lyophilizate thus obtained has a good aspect. Titer and purity of the lyophilizate is analyzed by HPLC, and compared to Scinopharm Fulvestrant used in the manufacture of the lyophilizate. HPLC determinations were carried out on an HPLC Waters with a Waters 1525 binary pump, Waters 717 autosampler, and a Waters 2996 diode array detector; the HPLC column used for determining titer and purity is an Agilent Eclipse XDB-C8 3.5 u 4.6×150 Rapid Res column; the chromatographic method corresponds to US Pharmacopeia (USP, 34 (2011)) monograph for Fulvestrant.

The titer of the lyophilizate was the same as that of Scinopharm Fulvestrant, 99.2%. Fulvestrant and lyophilizate total impurities were 0.1%.

Example 6

Lyophilization of Fulvestrant from Ethanol and Water at a Ratio of 1:2 by Volume To a 5 mL beaker, fitted with a magnetic stirrer, 0.5 mL Baker anhydrous ethanol is added with the aid of a 1000 uL Eppendorf Research micropipette.

The beaker was placed on an IKA MS2 Minishaker magnetic stirring plate, establishing plate conditions of agitation at 200 to 300 rpm.

Forty-nine Mg Fulvestrant from Scinopharm, lot#70850AA003 were weighed using an Ohaus model Adventurer balance.

Fulvestrant is slowly added. After all Fulvestrant was added stirring is continued for 5 minutes a clear solution was obtained. Then, with the aid of a 5000 uL Eppendorf Research micropipette, 1 mL of water is added. After the addition of water the solution is transformed into a suspension.

Stirring is stopped and with the aid of a 5 mL syringe and needle (Darling) the solution is dosed into an 11 mL type I glass vial from Nuova Ompi. The vial is pre-capped with a Helvoet Pharma bromobutyl lyophilization stopper and lyophilized using a Virtis Advantage lyophilizator. The lyophilization cycle is shown in table 6. Once the cycle is completed, vials are withdrawn from the lyophilizator, capped and crimped with aluminum seals.

TABLE 6

| Lyophilization Cycle | | | |
| --- | --- | --- | --- |
| Stage | Time (h) | Temperature (C.) | Working pressure |
| 1 | 22 | −50 | Higher than 60 mTorr |
| 2 | 6 | −50 | Lower than 60 mTorr |
| 3 | 15 | −40 | Lower than 60 mTorr |
| 4 | 9 | −30 | Lower than 60 mTorr |
| 5 | 7 | −20 | Lower than 60 mTorr |
| 6 | 11 | −10 | Lower than 60 mTorr |
| 7 | 9 | 0 | Lower than 60 mTorr |

The lyophilizate thus obtained has a good aspect. Titer and purity of the lyophilizate is analyzed by HPLC, and compared to Scinopharm Fulvestrant used in the manufacture of the lyophilizate. HPLC determinations were carried out on an HPLC Waters with a Waters 1525 binary pump, Waters 717 autosampler, and a Waters 2996 diode array detector; the HPLC column used for determining titer and purity is an Agilent Eclipse XDB-C8 3.5 u 4.6×150 Rapid Res column; the chromatographic method corresponds to US Pharmacopeia (USP, 34 (2011)) monograph for Fulvestrant.

The titer of the lyophilizate was the same as that of Scinopharm Fulvestrant, 99.2%. Fulvestrant and lyophilizate total impurities were 0.1%.

Example 7

Dissolution of the Lyophilizate

A 50 mL Schott, type I, glass vial is placed on an Ohaus Adventurer balance. Then, 3.12 g Merck ethanol, 4.17 g Sigma-Aldrich benzyl alcohol and 12.70 g Sigma-Aldrich castor oil are added.

With the aid of a 1000 uL Eppendorf Research micropipette, 5 mL of the previously prepared solvent was added into an 11 mL Nuova Ompi type I of glass vial. The vial is capped with a solution S-additive plug from WestPharma and crimped with an aluminum seal.

Figure 9:
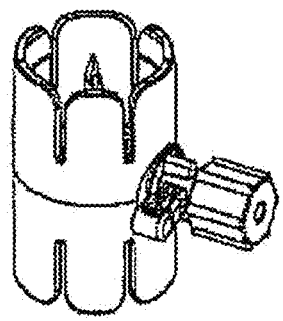
FIG. 9. Transfer system.

The process for reconstituting a vial of lyophilizate of example 1 with the solvent of said example, using a Needleless Transfer System Transfer Device 20/20 w/150 mic Filter Sterile from Westpharma, FIG. 9, is as follows:

1. Seals are removed from the containers (vials) containing the solid fulvestrant composition of the invention and the solubilizing composition.

2. The cover of the package containing the transfer system is removed.

3. The transfer system is placed on the top of the vial containing the solvent and the cap is pierced using one of the punches of the transfer system.

4. The vial with solvent is inverted together with the transfer device.

5. The transfer system is placed on top of the vial containing the lyophilizate and the cap is pierced using the free punch of the transfer system.

6. The protecting cover of the syringe of the transfer system is removed.

7. The protecting cover of the 10 mL Darling syringe is removed, and the syringe is introduced into the Luer lock of the transfer system.

8. The valve of the transfer system is mounted to remove the solvent, which is extracted with the syringe.

9. The transfer system valve is turned to connect the syringe and the lyophilizate.

10. The complete content of the syringe is discharged into the lyophilizate vial.

11. After the reconstituted solution is formed, the transfer system is turned 180 degrees to withdraw this solution with the aid of a syringe.

Using a Sper Scientific timer, it was determined that less than 90 seconds were required for reconstituting the lyophilizate.

Example 8

Dissolution of Solid API Fulvestrant

Using a 50 mL Schott type I glass vial, 250 mg Scinopharm Fulvestrant lot#70850AA003 are weighed.

With the aid of a 10 mL Darling syringe and needle, 5 mL of the solvent of example 7 are extracted and added to the vial containing Scinopharm API Fulvestrant.

It was determined that more than 60 minutes were required to completely dissolve Fulvestrant in the solvent using a Sper Scientific timer.

Example 9

Determination of Impurities in the Reconstituted Lyophilizate

Titer and purity of the reconstituted Fulvestrant of example 7 are analyzed by HPLC, and compared to Scinopharm Fulvestrant as used for manufacturing the lyophilizate. HPLC determinations were carried out on an HPLC Waters with a Waters 1525 binary pump, Waters 717 autosampler, and a Waters 2996 diode array detector; the HPLC column used for determining titer and purity is an Agilent Eclipse XDB-C8 3.5 u 4.6×150 Rapid Res column; the chromatographic method corresponds to US Pharmacopeia (USP, 34 (2011)) monograph for Fulvestrant.

The titer of the lyophilizate was the same as that of Scinopharm Fulvestrant, 99.2%. Fulvestrant and lyophilizate total impurities were 0.1%.

Example 10

Stability Test of the Fulvestrant Solution in Acetic Acid During 6 Hours at Room Temperature To a 10 mL beaker, fitted with a magnetic stirrer, 2.5 mL glacial acetic acid, Merck lot K 36685863, is added.

The beaker is placed on an IKA model MS2 Minishaker magnetic stirrer plate.

Fifty mg Fulvestrant from Scinopharm, lot#70850AA003 were weighed using an Ohaus model Adventurer balance.

Stirring of acetic acid is started and Fulvestrant is slowly added which is rapidly dissolved. After all Fulvestrant was added stirring is continued for 5 minutes.

Stirring is stopped and the solution is left at room temperature for 6 hours, then dissolution is analyzed in terms of titer and purity by HPLC, and compared to Scinopharm Fulvestrant as used for manufacturing the lyophilizate. HPLC determinations were carried out on an HPLC Waters with a Waters 1525 binary pump, Waters 717 autosampler, and a Waters 2996 diode array detector; the HPLC column used for determining titer and purity is an Agilent Eclipse XDB-C8 3.5 u 4.6×150 Rapid Res column; the chromatographic method corresponds to US Pharmacopeia (USP, 34 (2011)) monograph for Fulvestrant.

The titer of the solution was 99.2%, the same as the one of Scinopharm Fulvestrant, i.e. 99.2%. Fulvestrant and lyophilizate total impurities in the solution were 0.1%.

Example 11

Physical Characterization of Fulvestrant Manufactured by Scinopharm

The sample of Fulvestrant to be analyzed was manufactured by Scinopharm, lot#70850AA003. The physical characterization was made by X-ray diffraction, differential scanning calorimetry and thermogravimetric assays.

The X-ray assay was carried out in a Philips X'Pert with a PW3710 unity using CuKα radiation=1.54 A. Records were obtained in the range of $3°<2\theta<40°$. A step of $0.02°$ in $2\theta$ was used with a time counting of 2 seconds per step.

FIG. 1 shows a diffraction diagram of the sample which has a typical diffraction pattern corresponding to a crystalline sample.

The differential scanning calorimetry assay was performed with a Shimadzu DSC 60. A sample of 1.68 mg was placed on an aluminum sampleholder, and heated at 10° C./min from room temperature to 200° C. Work was carried out under $N_2$ with a flow of 30 mL/min.

Figure 2:
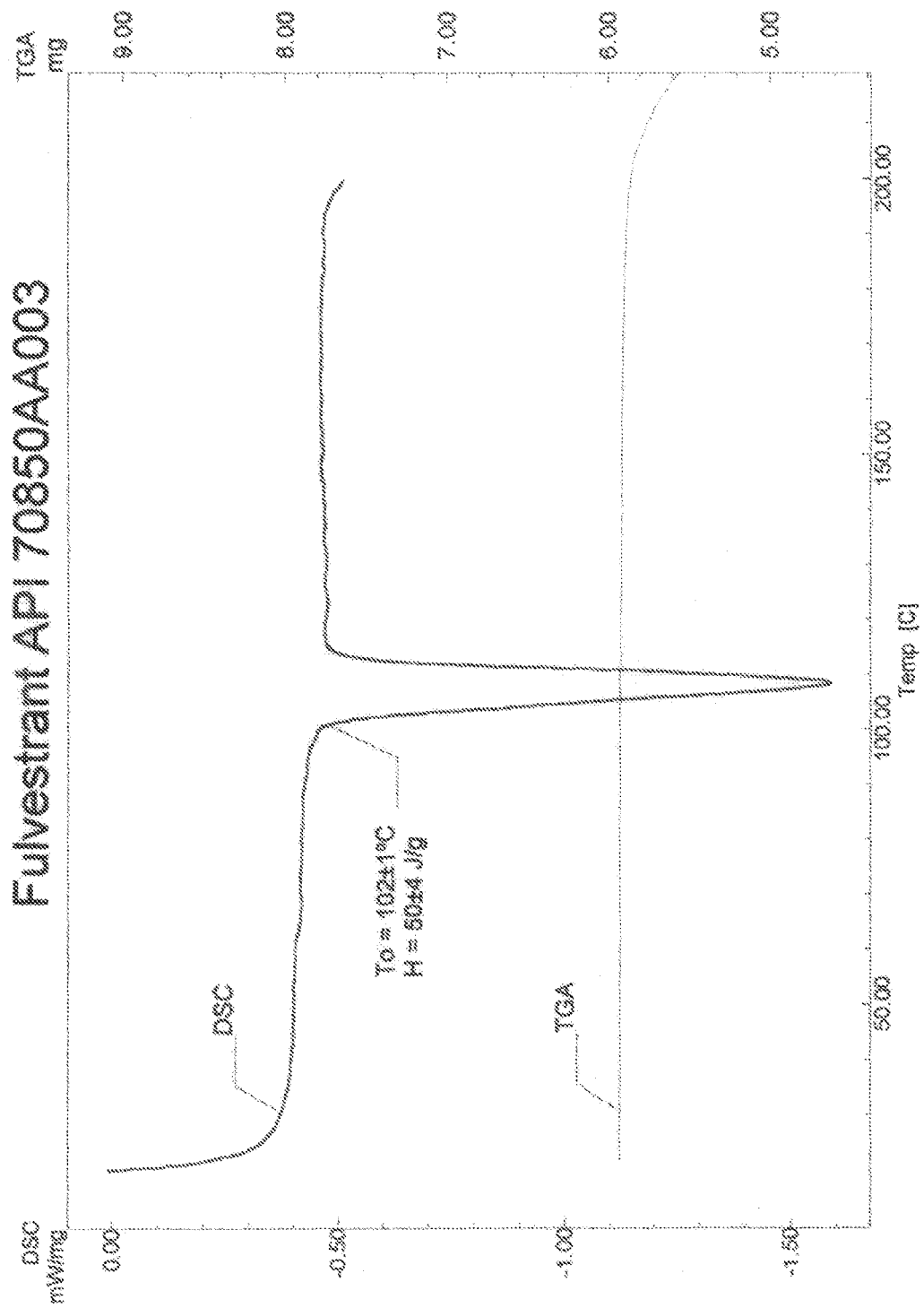
FIG. 2. Thermogram and thermogravimetry of Scinopharm Fulvestrant.

The thermogravimetric assay was performed with a Shimadzu TG 50. The sample was placed in an aluminum sampleholder. It was heated from room temperature to 400° C. with heating rate of 10° C./min, under dry air flow of 40 mL/min FIG. 2 shows a differential scanning calorimetry diagram and a thermogravimetric diagram. An endothermic signal characterized by an onset temperature To=49+/−1° C. and an enthalpy variation of 11+/−2 J/g was observed, which as may be appreciated in the thermogravimetric diagram does not correspond to mass loss and presumably corresponds to the melting point, which confirms that the crystalline state of fulvestrant is a crystal.

Example 12

Physical Characterization of Fulvestrant Manufactured by Sicor

The sample of Fulvestrant to be analyzed was manufactured by Sicor, lot#4233500210C. The physical characterization was made by X-ray diffraction, differential scanning calorimetry and thermogravimetric assays.

The X-ray assay was carried out in a Philips X'Pert with a PW3710 unity using CuKα radiation=1.54 A. Records were obtained in the range of $3°<2\theta<40°$. A step of $0.02°$ in $2\theta$ was used with a time counting of 2 seconds per step.

Figure 3:
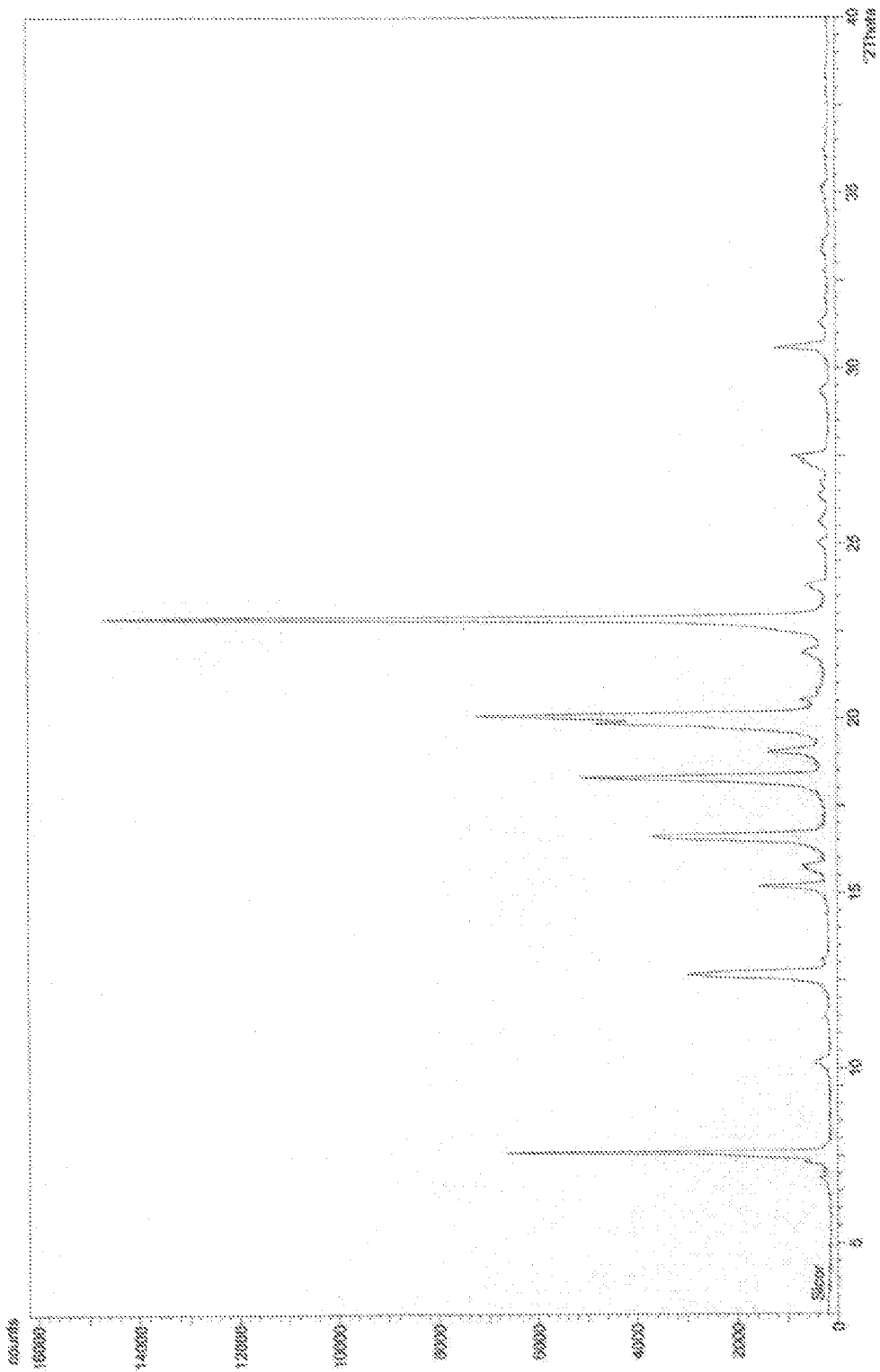
FIG. 3. X-Ray diffraction diagram of Sicor Fulvestrant.

FIG. 3 shows a diffraction diagram of the sample which has a typical diffraction pattern corresponding to a crystalline sample.

The differential scanning calorimetry assay was performed with a Shimadzu DSC 60. A sample of 2.82 mg was placed on an aluminum sampleholder, and heated at 10° C./min from room temperature to 200° C. Work was carried out under $N_2$ with a flow of 30 mL/min.

Figure 4:
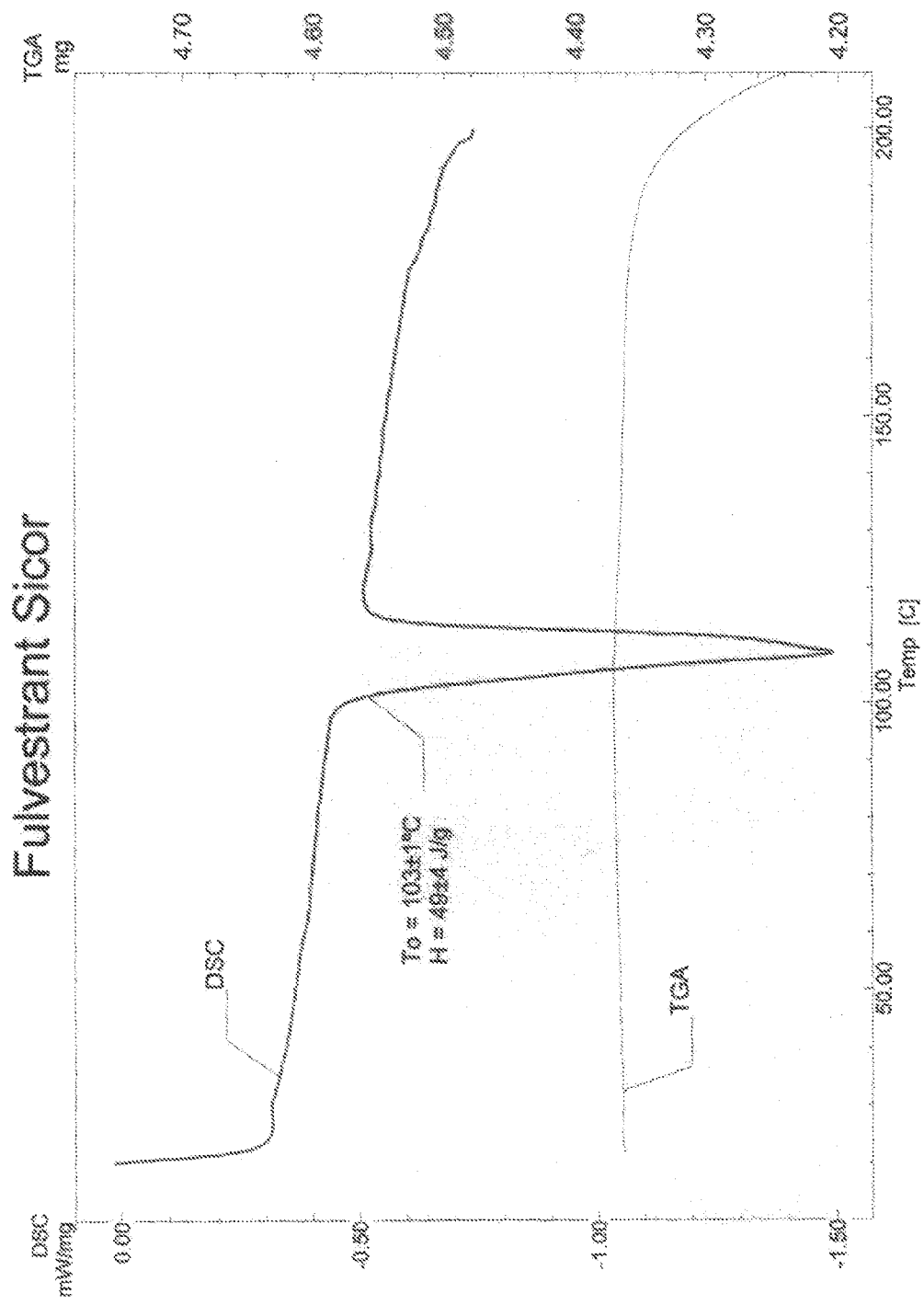
FIG. 4. Thermogram and thermogravimetry of Sicor Fulvestrant.

The thermogravimetric assay was performed with a Shimadzu TG 50. The sample was placed in an aluminum sampleholder. It was heated from room temperature to 400° C. with heating rate of 10° C./min, under dry air flow of 40 mL/min FIG. 4 shows a differential scanning calorimetry diagram and a thermogravimetric diagram. An endothermic signal characterized by an onset temperature To=103+/−1° C. and an enthalpy variation of 49+/−2 J/g was observed, which as may be appreciated in the thermogravimetric diagram does not correspond to mass loss and presumably corresponds to the melting point, which confirms that the crystalline state of fulvestrant is a crystal.

It may be appreciated upon comparing the results of Scinopharm and Sicor Fulvestrant that the X-ray diffraction diagram, the melting point and fusion enthalpy are very similar.

Example 13

Syringeability and Injectability of Different Solvents Using Needles and Using a Transfer System Syringeability and injectability are key parameters for the design of parenteral products. The first term refers to the ability of the injectable to readily pass through a needle when transferred from one vial to another; the second term refers to the ability to be injected. The syringeability includes factors such as easy extraction, obstruction and foam formation as well as precision of metered doses. The injectability includes the pressure or force required for the injection, flow uniformity and non-obstruction (13).

The syringeability of the solvent and the reconstituted solution of example 7 were assayed using 3 systems: the first system consisted of a 10 mL Darling syringe, with 23 G needles, the second system employed a 10 mL Darling syringe, with 18 G needles, both needles had a length of 3.8 cm, and the last one was the transfer system described in example 7.

The assay consisted in extracting the solvent describe in example 7, injecting it in the lyophilizate vial, reconstituting the lyophilizate and extracting it from the vial containing it.

When the solvent extraction assay was carried out with the syringe and 23 G needle system we discovered that no solvent could be extracted. This is due to the high viscosity of the solvent and the high caliper of the syringe. Therefore it was decided to use a syringe with lower needle caliper, i.e. having a greater diameter hole of the needle, performing the assay with an 18 G needle. But the result was the same as before, nothing could be extracted.

The selection of a 23 G needle is supported by the fact that the reconstituted Fulvestrant, like the original product Faslodex, is administered intramuscularly. According to reference (14), needles comprising from 21 to 23 G and with a length from 2.5 cm to 3.8 cm should be used for intramuscular injections; a 23 G needle is used for the original product, Faslodex.

The use of a transfer system, another object of the present invention, allowed for passing solvent to the syringe, from the syringe to the reconstitution vial and from the latter to the syringe almost immediately and with no need to exert any force.

REFERENCES

1 G. W. Oetjen; *Freeze-Drying*; Pag 1, Wiley-VCH, 1999.
2 D. L. Teagarden, D. S. Baker, *Practical aspects of lyophilization using non-aqueous co-solvent systems; European Journal of Pharmaceutical Sciences*, 15, 115-133, 2002.
3 U.S. Pat. No. 6,774,122.
4 L. Rey, J. May; *Freeze Drying/Lyophilization of Pharmaceutical and Biological Products*, 3 edition; *Informa Healthcare; p.* 25, 2010.
5 L. Rey, J. May: *Freeze Drying/Lyophilization of Pharmaceutical and Biological Products*, 3 edition; *Informa Healthcare, p.* 325, 2010.
6 T. A. Jennings: *Lyophilization Introduction and Basic Principles; Informa Healthcare*, p. 428, 2008.
7 US Application 2009/0227549
8 Insert of Faslodex
9 http://www.brooksidepress.org/Products/Administer_IM_SQ_and_ID_Injections/lesson_2_Section_2.htm
10 Scientific Discussion EMEA 2005
11 David E. Alonso et al.: *Understanding the Behavior of Amorphous Pharmaceutical Systems during Dissolution; Pharmaceutical Research*, 27, 4, 2010
12 Sharad B. Murdande et al.: *Solubility Advantage of Amorphous Pharmaceuticals: II; Application of Quantitative Thermodynamic Relationships for Prediction of Solubility Enhancement in Structural Diverse Insoluble Pharmaceuticals; Pharmaceutical Research*, 27, 2704-2714, 2010.
13 F. Cilurzo et al.; *Injectability Evaluation: An Open Issue; AAPS PharmSciTech* 07/005/2011.
14 http://www.thenursingsite.com/Articles/how%20to%20determine%20needle%20size%20for-%20injection.htm Having thus specifically described and determined the nature and the best mode for carrying out the present invention, we claim property and exclusive right as follows:

1. A solid pharmaceutical composition comprising amorphous fulvestrant, wherein the amorphous fulvestrant has a broad X-ray diffraction image with a maximum in a $2\theta$ from $15°$ to $20°$.

2. The composition of claim 1 characterized in that said solid composition is lyophilized.

3. The composition of claim 2 characterized in that said solid composition is lyophilized from a solution of the pharmaceutical active principle fulvestrant in a lyophilization solvent selected from the group consisting of acetic acid, dimethylsufoxide, tert-butanol, and mixtures thereof.

4. The composition of claim 2 characterized in that said lyophilized composition has a purity of at least 95%.

5. The composition of claim 1 characterized in that said composition is soluble in a solution of castor oil, alcohol and no benzyl benzoate, over a time period of less than 180 seconds.

6. The composition of claim 1 characterized in that said composition is soluble in a solution of castor oil, alcohol and no benzyl benzoate, over a time period of less than 90 seconds.

7. A kit characterized by comprising: a first container containing the solid fulvestrant composition of claim 1; a second container containing a solubilizing composition for said solid fulvestrant composition; and a syringe.

8. The kit of claim 7 characterized in that said syringe is prefilled and comprises said first container and said second container.

9. A kit according to claim 7 and a transfer system connecting said containers with said syringe.

10. Process for obtaining the composition of claim 1 comprising the steps of:
   a. dissolving the active pharmaceutical principle fulvestrant in a lyophilization solvent selected from the group consisting of acetic acid, dimethylsulfoxide, tert-butanol and mixtures thereof,
   b. drying the resulting solution.

11. The process of claim 10 characterized in that step b comprises lyophilization.

12. The process of claim 10 characterized in that said solid composition contains less than 0.5% of organic solvents.

* * * * *